(12) United States Patent
Schauer et al.

(10) Patent No.: US 12,171,994 B2
(45) Date of Patent: Dec. 24, 2024

(54) REDUCED THROMBOSIS BLOOD PUMP WITH WASHOUT BEARING

(71) Applicant: Boston Scientific Scimed Inc., Maple Grove, MN (US)

(72) Inventors: Travis J. Schauer, Rockford, MN (US); Benjamin Breidall, Eden Prairie, MN (US); Daniel H. VanCamp, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 74 days.

(21) Appl. No.: 17/016,961

(22) Filed: Sep. 10, 2020

(65) Prior Publication Data

US 2021/0069393 A1 Mar. 11, 2021

Related U.S. Application Data

(60) Provisional application No. 62/898,953, filed on Sep. 11, 2019.

(51) Int. Cl.
*A61M 60/825* (2021.01)
*A61M 60/148* (2021.01)
*A61M 60/422* (2021.01)

(52) U.S. Cl.
CPC ........ *A61M 60/825* (2021.01); *A61M 60/422* (2021.01); *A61M 60/148* (2021.01)

(58) Field of Classification Search
CPC .............. A61M 60/818; A61M 60/422; A61M 60/148; A61M 60/221; A61M 60/126; A61M 60/825
See application file for complete search history.

(56) References Cited

U.S. PATENT DOCUMENTS

| | | | |
|---|---|---|---|
| 4,277,706 A | * | 7/1981 | Isaacson ............. A61M 60/443 310/83 |
| 4,817,586 A | | 4/1989 | Wampler |
| 4,944,722 A | | 7/1990 | Carriker et al. |
| 5,211,546 A | * | 5/1993 | Isaacson ............. A61M 60/806 604/151 |
| 5,527,159 A | | 6/1996 | Bozeman, Jr. et al. |
| 5,692,882 A | | 12/1997 | Bozeman, Jr. et al. |
| 5,947,892 A | | 9/1999 | Benkowski et al. |
| 5,964,694 A | | 10/1999 | Siess et al. |
| 6,007,478 A | | 12/1999 | Siess et al. |
| 6,093,001 A | | 7/2000 | Burgreen et al. |

(Continued)

FOREIGN PATENT DOCUMENTS

| | | |
|---|---|---|
| EP | 0847767 B1 | 2/2005 |
| EP | 2301598 B1 | 5/2017 |
| EP | 3352808 B1 | 9/2023 |

*Primary Examiner* — Yingchuan Zhang
*Assistant Examiner* — Sebastian X Lukjan
(74) *Attorney, Agent, or Firm* — Seager, Tufte & Wickhem LLP

(57) ABSTRACT

A bearing assembly is configured to retain an end of an impeller of a blood pump and includes a thrust plate having a distal-facing surface and an impeller bearing surface configured to be disposed adjacent the distal-facing surface such that a gap is defined between the distal-facing surface of the thrust plate and the impeller bearing surface. The impeller bearing surface includes at least one washout blade disposed thereon and configured to facilitate blood flow through the gap.

19 Claims, 4 Drawing Sheets

(56) References Cited

U.S. PATENT DOCUMENTS

| | | |
|---|---|---|
| 6,123,659 A | 9/2000 | Le Blanc et al. |
| 6,135,729 A | 10/2000 | Aber |
| 6,139,487 A | 10/2000 | Siess |
| 6,176,822 B1 | 1/2001 | Nix et al. |
| 6,176,848 B1 | 1/2001 | Rau et al. |
| 6,186,665 B1 | 2/2001 | Maher et al. |
| 6,227,817 B1 | 5/2001 | Paden |
| 6,227,820 B1 | 5/2001 | Jarvik |
| 6,234,772 B1 | 5/2001 | Wampler et al. |
| 6,254,359 B1 | 7/2001 | Aber |
| 7,011,620 B1 | 3/2006 | Siess |
| 7,731,675 B2 | 6/2010 | Aboul-Hosn et al. |
| 7,841,976 B2 | 11/2010 | McBride et al. |
| 7,927,068 B2 | 4/2011 | McBride et al. |
| 7,972,122 B2 | 7/2011 | LaRose et al. |
| 8,376,707 B2 | 2/2013 | McBride et al. |
| 8,449,443 B2 | 5/2013 | Rodefeld et al. |
| 8,506,470 B2 | 8/2013 | LaRose et al. |
| 8,591,393 B2 | 11/2013 | Walters et al. |
| 8,597,170 B2 | 12/2013 | Walters et al. |
| 8,684,904 B2 | 4/2014 | Campbell et al. |
| 8,721,517 B2 | 5/2014 | Zeng et al. |
| 8,992,163 B2 | 3/2015 | McBride et al. |
| 9,138,518 B2 | 9/2015 | Campbell et al. |
| 9,308,302 B2 | 4/2016 | Zeng |
| 9,308,304 B2 | 4/2016 | Peters et al. |
| 9,327,067 B2 | 5/2016 | Zeng et al. |
| 9,364,592 B2 | 6/2016 | McBride et al. |
| 9,364,593 B2 | 6/2016 | McBride et al. |
| 9,381,288 B2 | 7/2016 | Schenck et al. |
| 9,421,311 B2 | 8/2016 | Tanner et al. |
| 9,446,179 B2 | 9/2016 | Keenan et al. |
| 9,561,313 B2 | 2/2017 | Taskin |
| 9,675,740 B2 | 6/2017 | Zeng et al. |
| 9,717,832 B2 | 8/2017 | Taskin et al. |
| 9,717,833 B2 | 8/2017 | McBride et al. |
| 9,759,229 B2 | 9/2017 | Baumgartner et al. |
| 9,770,543 B2 | 9/2017 | Tanner et al. |
| 9,771,801 B2 | 9/2017 | Schumacher et al. |
| 9,872,947 B2 | 1/2018 | Keenan et al. |
| 9,895,476 B2 | 2/2018 | LaRose et al. |
| 9,907,890 B2 | 3/2018 | Muller |
| 9,956,332 B2 | 5/2018 | LaRose et al. |
| 9,962,475 B2 | 5/2018 | Campbell et al. |
| 10,029,037 B2 | 7/2018 | Muller et al. |
| 10,039,872 B2 | 8/2018 | Zeng et al. |
| 10,071,192 B2 | 9/2018 | Zeng |
| 10,086,121 B2 | 10/2018 | Fitzgerald et al. |
| 10,105,475 B2 | 10/2018 | Muller |
| 10,117,980 B2 | 11/2018 | Keenan et al. |
| 10,149,932 B2 | 12/2018 | McBride et al. |
| 10,215,187 B2 | 2/2019 | McBride et al. |
| 10,232,099 B2 | 3/2019 | Peters et al. |
| 10,251,985 B2 | 4/2019 | Larose et al. |
| 10,251,986 B2 | 4/2019 | Larose et al. |
| 10,265,448 B2 | 4/2019 | Liebing |
| 10,478,539 B2 | 11/2019 | Pfeffer et al. |
| 10,525,178 B2 | 1/2020 | Zeng |
| 10,576,192 B2 | 3/2020 | Muller et al. |
| 10,576,193 B2 | 3/2020 | Tanner et al. |
| 10,702,641 B2 | 7/2020 | Lee et al. |
| 10,709,829 B2 | 7/2020 | Muller |
| 10,709,830 B2 | 7/2020 | Tanner et al. |
| 10,722,627 B1 * | 7/2020 | Obeid ................. F16C 33/1075 |
| 10,724,534 B2 | 7/2020 | Woo et al. |
| 10,765,789 B2 | 9/2020 | Zeng et al. |
| 10,773,002 B2 | 9/2020 | Siess et al. |
| 10,780,208 B2 | 9/2020 | Siess et al. |
| 10,786,610 B2 | 9/2020 | Zeng |
| 10,799,624 B2 | 10/2020 | Pfeffer et al. |
| 10,842,921 B2 | 11/2020 | Siess et al. |
| 10,864,308 B2 | 12/2020 | Muller et al. |
| 10,864,309 B2 | 12/2020 | McBride et al. |
| 10,874,783 B2 | 12/2020 | Pfeffer et al. |
| 10,894,115 B2 | 1/2021 | Pfeffer et al. |
| 10,918,774 B2 | 2/2021 | Stanfield et al. |
| 10,960,116 B2 | 3/2021 | Campbell et al. |
| 10,980,927 B2 | 4/2021 | Pfeffer et al. |
| 11,058,865 B2 | 7/2021 | Fitzgerald et al. |
| 11,097,092 B2 | 8/2021 | Siess et al. |
| 11,103,689 B2 | 8/2021 | Siess et al. |
| 11,123,539 B2 | 9/2021 | Pfeffer et al. |
| 11,129,978 B2 | 9/2021 | Pfeffer et al. |
| 11,167,124 B2 | 11/2021 | Pfeffer et al. |
| 11,229,786 B2 | 1/2022 | Zeng et al. |
| 11,235,138 B2 | 2/2022 | Gross-Hardt et al. |
| 11,253,693 B2 | 2/2022 | Pfeffer et al. |
| 11,260,213 B2 | 3/2022 | Zeng et al. |
| 11,273,301 B2 | 3/2022 | Pfeffer et al. |
| 11,311,712 B2 | 4/2022 | Zeng et al. |
| 11,313,228 B2 | 4/2022 | Schumacher et al. |
| 11,338,124 B2 | 5/2022 | Pfeffer et al. |
| 11,357,967 B2 | 6/2022 | Zeng et al. |
| 11,400,276 B2 | 8/2022 | Chopra et al. |
| 11,497,896 B2 | 11/2022 | Tanner et al. |
| 11,517,736 B2 | 12/2022 | Earles et al. |
| 11,565,103 B2 | 1/2023 | Farago et al. |
| 11,583,659 B2 | 2/2023 | Pfeffer et al. |
| 11,628,294 B2 | 4/2023 | Chopra et al. |
| 11,666,748 B2 | 6/2023 | Kronstedt et al. |
| 11,708,833 B2 | 7/2023 | McBride et al. |
| 11,754,075 B2 | 9/2023 | Schuelke et al. |
| 11,786,700 B2 | 10/2023 | Pfeffer et al. |
| 2004/0241019 A1 * | 12/2004 | Goldowsky ......... A61M 60/824 |
| | | 417/423.12 |
| 2008/0114339 A1 | 5/2008 | McBride et al. |
| 2009/0060743 A1 | 3/2009 | McBride et al. |
| 2010/0249489 A1 | 9/2010 | Jarvik |
| 2012/0178985 A1 | 7/2012 | Walters et al. |
| 2012/0178986 A1 | 7/2012 | Campbell et al. |
| 2013/0096364 A1 | 4/2013 | Reichenbach et al. |
| 2015/0051436 A1 * | 2/2015 | Spanier ................ A61M 60/13 |
| | | 600/16 |
| 2016/0193396 A1 * | 7/2016 | Taskin ................ A61M 60/806 |
| | | 600/16 |
| 2016/0279310 A1 | 9/2016 | Scheckel et al. |
| 2017/0128646 A1 | 5/2017 | Karch |
| 2017/0296725 A1 | 10/2017 | Peters et al. |
| 2018/0050139 A1 * | 2/2018 | Siess ................... A61M 60/824 |
| 2018/0169312 A1 * | 6/2018 | Barry .................. A61M 60/148 |
| 2018/0228953 A1 * | 8/2018 | Siess ................... A61M 60/825 |
| 2018/0311421 A1 * | 11/2018 | Tuseth ................ A61M 60/178 |
| 2018/0311423 A1 | 11/2018 | Zeng et al. |
| 2018/0311425 A1 * | 11/2018 | Tuseth ................ A61M 60/178 |
| 2019/0125948 A1 * | 5/2019 | Stanfield ............. A61M 60/205 |
| 2020/0306434 A1 | 10/2020 | VanCamp et al. |
| 2021/0015981 A1 * | 1/2021 | Kirchhoff ........... A61M 60/148 |
| 2021/0015982 A1 | 1/2021 | Kerkhoffs et al. |
| 2021/0038785 A1 | 2/2021 | Siess et al. |
| 2021/0106810 A1 | 4/2021 | Pfeffer et al. |
| 2021/0113825 A1 | 4/2021 | Kirchhoff et al. |
| 2022/0134082 A1 | 5/2022 | Pfeffer et al. |

* cited by examiner

REDUCED THROMBOSIS BLOOD PUMP WITH WASHOUT BEARING

CROSS REFERENCE TO RELATED APPLICATION

This application claims priority to Provisional Application No. 62/898,953, filed Sep. 11, 2019, which is herein incorporated by reference in its entirety.

TECHNICAL FIELD

The present disclosure relates to percutaneous circulatory support devices. More specifically, the disclosure relates to bearings using in percutaneous circulatory support devices.

BACKGROUND

Percutaneous circulatory support devices such as blood pumps provide circulatory support. Stagnant blood areas in and around bearings are prone to thrombus formation.

SUMMARY

In an Example 1, a bearing assembly configured to retain an end of an impeller of a blood pump comprises a thrust plate having a distal-facing surface; and an impeller bearing surface configured to be disposed adjacent the distal-facing surface such that a gap is defined between the distal-facing surface of the thrust plate and the impeller bearing surface, the impeller bearing surface having disposed thereon at least one washout blade configured to facilitate blood flow through the gap.

In an Example 2, the bearing assembly of Example 1, wherein the at least one washout blade comprises two or more washout blades.

In an Example 3, the bearing assembly of either of Examples 1 or 2, wherein the at least one washout blade extends radially outward.

In an Example 4, the bearing assembly of any of Examples 1-3, wherein the at least one washout blade is forward-swept with respect to a direction of rotation of the impeller bearing surface.

In an Example 5, the bearing assembly of any of Examples 1-3, wherein the at least one washout blade is backward-swept with respect to a direction of rotation of the impeller bearing surface.

In an Example 6, the bearing assembly of any of Examples 1-5, wherein the at least one washout blade is curved.

In an Example 7, the bearing assembly of any of Examples 1-6, wherein the impeller bearing surface comprises a proximal surface of the impeller.

In an Example 8, the bearing assembly of any of Example 1-6, wherein the impeller bearing surface comprises a proximal surface of a magnet cover that is configured to be disposed over at least a proximal surface of a rotor magnet.

In an Example 9, the bearing assembly of any of Examples 1-8, wherein a height of the at least one washout blade, comprising a distance from the impeller bearing surface to a proximal edge of the at least one washout blade, is approximately half the width of the gap.

In an Example 10, a blood pump comprises: an impeller; a motor configured to drive the impeller; and a bearing assembly disposed adjacent the motor and configured to receive a proximal end of the impeller, the bearing assembly comprising a thrust plate having a distal-facing surface, and an impeller bearing surface configured to be disposed adjacent the distal-facing surface such that a gap is defined between the distal-facing surface of the thrust plate and the impeller bearing surface, the impeller bearing surface having disposed thereon at least one washout blade configured to facilitate blood flow through the gap.

In an Example 11, the blood pump of Example 10, wherein the at least one washout blade comprises two or more washout blades.

In an Example 12, the blood pump of either of Examples 10 or 11, wherein the at least one washout blade is curved.

In an Example 13, the blood pump of any of Examples 10-12, wherein the impeller bearing surface comprises a proximal surface of the impeller.

In an Example 14, the blood pump of any of Examples 10-13, wherein the impeller bearing surface comprises a proximal surface of a magnet cover that is configured to be disposed over at least a proximal surface of a rotor magnet.

In an Example 15, the blood pump of any of Examples 10-13, wherein a height of the at least one washout blade, comprising a distance from the impeller bearing surface to a proximal edge of the at least one washout blade, is approximately half the width of the gap.

In an Example 16, a bearing assembly configured to retain an end of an impeller of a blood pump, the bearing assembly comprising: a thrust plate having a distal-facing surface; and an impeller bearing surface configured to be disposed adjacent the distal-facing surface such that a gap is defined between the distal-facing surface of the thrust plate and the impeller bearing surface, the impeller bearing surface having disposed thereon at least one washout blade configured to facilitate blood flow through the gap.

In an Example 17, the bearing assembly of Example 16, wherein the at least one washout blade comprises two or more washout blades.

In an Example 18, the bearing assembly of Example 16, wherein the at least one washout blade extends radially outward.

In an Example 19, The bearing assembly of Example 16, wherein the at least one washout blade is forward-swept with respect to a direction of rotation of the impeller bearing surface.

In an Example 20, the bearing assembly of Example 16, wherein the at least one washout blade is backward-swept with respect to a direction of rotation of the impeller bearing surface.

In an Example 21, the bearing assembly of Example 16, wherein the at least one washout blade is curved.

In an Example 22, the bearing assembly of Example 16, wherein the impeller bearing surface comprises a proximal surface of the impeller.

In an Example 23, the bearing assembly of Example 16, wherein the impeller bearing surface comprises a proximal surface of a magnet cover that is configured to be disposed over at least a proximal surface of a rotor magnet.

In an Example 24, The bearing assembly of Example 16, wherein a height of the at least one washout blade, comprising a distance from the impeller bearing surface to a proximal edge of the at least one washout blade, is approximately half the width of the gap.

In an Example 25, a blood pump, comprising: an impeller; a motor configured to drive the impeller; and a bearing assembly disposed adjacent the motor and configured to receive a proximal end of the impeller, the bearing assembly comprising a thrust plate having a distal-facing surface, and an impeller bearing surface configured to be disposed adjacent the distal-facing surface such that a gap is defined between the distal-facing surface of the thrust plate and the impeller bearing surface, the impeller bearing surface having disposed thereon at least one washout blade configured to facilitate blood flow through the gap.

In an Example 26, the blood pump of Example 25, wherein the at least one washout blade comprises two or more washout blades.

In an Example 27, the blood pump of Example 25, wherein the at least one washout blade extends radially outward.

In an Example 28, the blood pump of Example 25, wherein the at least one washout blade is forward-swept with respect to a direction of rotation of the impeller bearing surface.

In an Example 29, the blood pump of Example 25, wherein the at least one washout blade is backward-swept with respect to a direction of rotation of the impeller bearing surface.

In an Example 30, the blood pump of Example 25, wherein the at least one washout blade is curved.

In an Example 31, the blood pump of Example 25, wherein the impeller bearing surface comprises a proximal surface of the impeller.

In an Example 32, the blood pump of Example 25, wherein the impeller bearing surface comprises a proximal surface of a magnet cover that is configured to be disposed over at least a proximal surface of a rotor magnet.

In an Example 33, the blood pump of Example 25, wherein a height of the at least one washout blade, comprising a distance from the impeller bearing surface to a proximal edge of the at least one washout blade, is approximately half the width of the gap.

In an Example 34, a blood pump, comprising: an impeller; a motor configured to drive the impeller; and a bearing assembly disposed adjacent the motor and configured to receive a proximal end of the impeller, the bearing assembly comprising a thrust plate having a distal-facing surface, and an impeller bearing surface configured to be disposed adjacent the distal-facing surface such that a gap is defined between the distal-facing surface of the thrust plate and the impeller bearing surface, the impeller bearing surface having disposed thereon two or more washout blades configured to facilitate blood flow through the gap, wherein the width of the gap is configured to maximize the blood flow through the gap.

In an Example 35, the blood pump of Example 34, wherein the impeller bearing surface comprises a proximal surface of the impeller.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

Figure 1A:
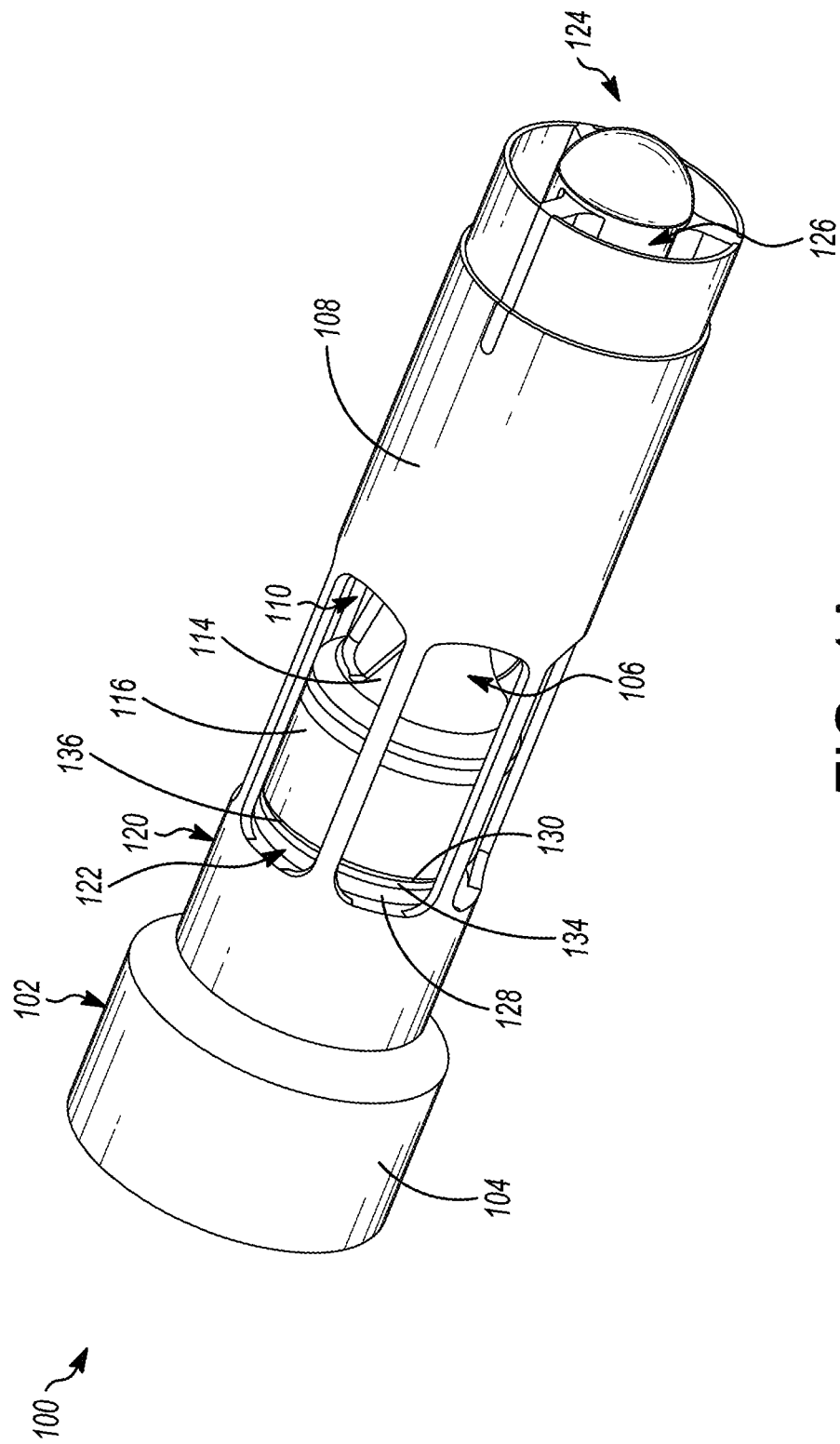
FIG. 1A depicts a perspective view of a portion of an illustrative percutaneous mechanical circulatory support device (also referred to herein, interchangeably, as a "blood pump"), in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

DETAILED DESCRIPTION

Embodiments of the subject matter disclosed herein include blood pump designs that facilitate blood flow through a proximal bearing to eliminate stagnant regions, thereby reducing, for example, thrombus formation. In embodiments, one or more washout blades are disposed on a proximal end of an impeller assembly and, as the impeller assembly rotates, the one or more washout blades cause blood to be drawn into, and pushed out of, a gap between the proximal surface of the impeller assembly and a distal-facing surface of a bearing. In other embodiments, the impeller assembly may be provided without washout blades, but where the gap is configured such that the rotation of the impeller assembly, in contrast with the stationary bearing surface, causes flow of blood into and out of the gap. As the terms "proximal" and "distal" are used herein, "proximal" refers to the general direction opposite that of insertion—that is, the direction in which one would travel along the device to exit the subject's body; whereas distal refers to the general direction of implantation—that is, the direction in which one would travel along the device to reach the end of the device that is configured to advance into the subject's body.

Figure 1B:
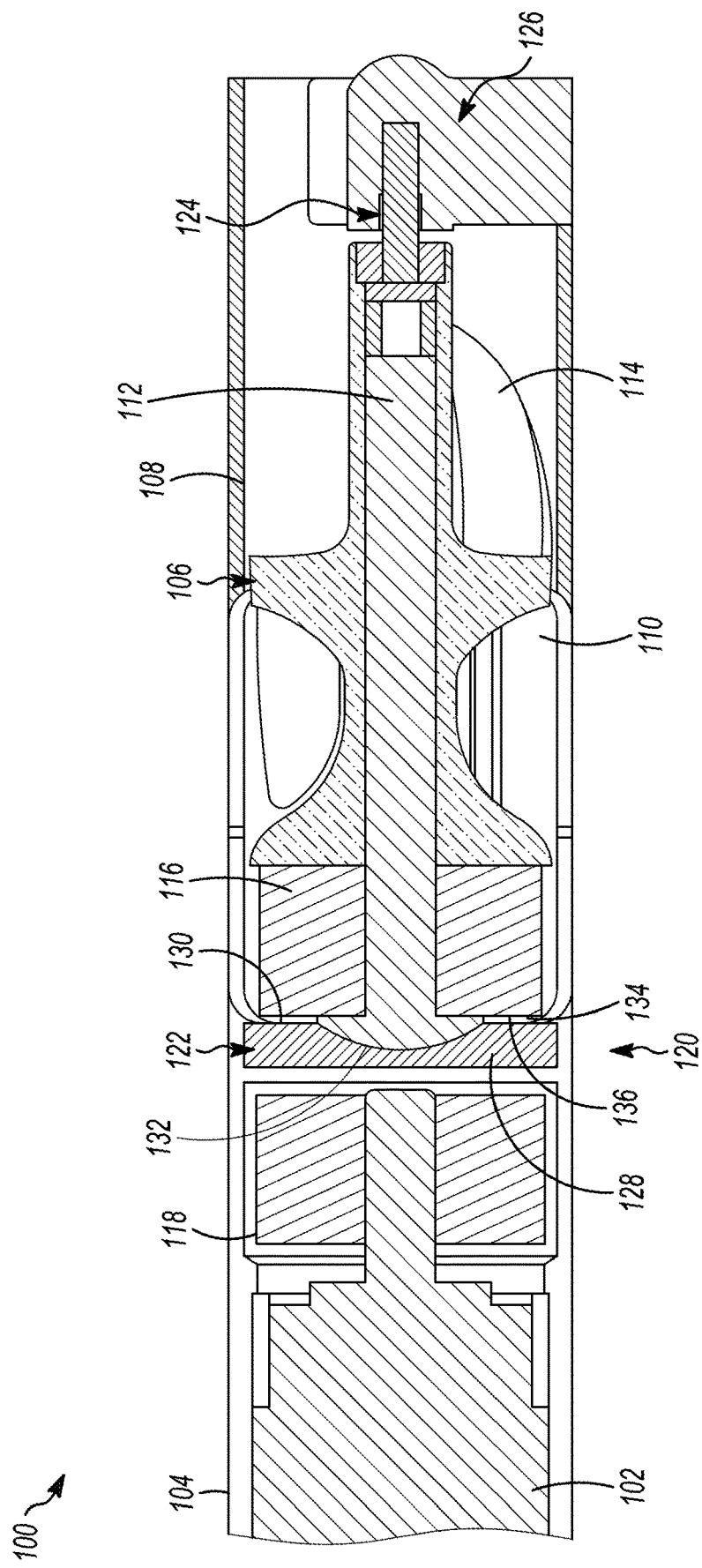
FIG. 1B depicts a cross-sectional side view of the circulatory support device depicted in FIG. 1A, in accordance with embodiments of the subject matter disclosed herein.

FIG. 1A depicts a perspective view of a portion of an illustrative percutaneous mechanical circulatory support device 100 (also referred to herein, interchangeably, as a "blood pump"), and FIG. 1B depicts a cross-sectional side view of the circulatory support device 100 depicted in FIG. 1A, in accordance with embodiments of the subject matter disclosed herein. As shown in FIGS. 1A and 1B, the circulatory support device 100 includes a motor 102 disposed within a motor housing 104. The motor 102 is configured to drive an impeller assembly 106 to provide a flow of blood through the device 100. The impeller assembly 106 is disposed within an impeller assembly housing 108, which includes a number of outlet apertures 110 defined therein. According to embodiments, the motor housing 104 and the impeller assembly housing 108 may be integrated with one another. In other embodiments, the motor housing 104 and the impeller assembly housing 108 may be separate components configured to be coupled together, either removeably or permanently.

A controller (not shown) is operably coupled to the motor 102 and is configured to control the motor 102. The controller may be disposed within the motor housing 104 in embodiments, or, in other embodiments, may be disposed outside the housing 104 (e.g., in a catheter handle, independent housing, etc.). In embodiments, the controller may include multiple components, one or more of which may be disposed within the housing 104. According to embodiments, the controller may be, include, or be included in one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors), one or more central processing units (CPUs), software, hardware, firmware, or any combination of these and/or other components. Although the controller is referred to herein in the singular, the controller may be implemented in multiple instances, distributed across multiple computing devices, instantiated within multiple virtual machines, and/or the like.

As shown in FIG. 1B, the impeller assembly 106 includes a drive shaft 112 and an impeller 114 coupled thereto, where the drive shaft 112 is configured to rotate with the impeller 114. As shown, the drive shaft 112 is at least partially disposed within the impeller 114. In embodiments, the drive shaft 112 may be made of any number of different rigid materials such as, for example, steel, titanium alloys, cobalt chromium alloys, nitinol, high-strength ceramics, and/or the like. The impeller assembly 106 further includes an impeller rotor 116 coupled to the impeller 114. The impeller rotor 116 may additionally, or alternatively, be coupled to the drive shaft 112. The impeller rotor 116 may be any type of magnetic rotor capable of being driven by a stator 118 that is part of the motor 102. In this manner, as a magnetic field is applied to the impeller rotor 116 by the stator 118 in the motor 102, the rotor 116 rotates, causing the impeller 114 to rotate.

As shown, the impeller assembly 106 is maintained in its orientation by being retained, at a first, proximal end 120, by a first (proximal) bearing assembly 122 and, at a second, distal end 124, by a second (distal) bearing assembly 126. According to embodiments, the proximal bearing assembly 122 and the distal bearing assembly 126 may include different types of bearings. According to embodiments, the proximal bearing assembly 122 and/or the distal bearing assembly 126 may include lubrication, while, in other embodiments, one and/or the other may not include lubrication.

According to embodiments, the proximal bearing assembly 122 may include a thrust plate 128 having a distal-facing surface 130, a portion of which is configured to engage an impeller bearing surface 132 of the drive shaft 112. A gap 134 may be formed between the distal-facing surface 130 and a proximal surface 136 of the impeller assembly 106. In embodiments, the impeller bearing surface 132 and the proximal surface 136 may be integrated. In embodiments, the proximal surface 136 may include a proximal surface of a magnet cover that is configured to be disposed over at least a proximal surface of the rotor 116. In other embodiments (e.g., in direct-drive implementations), the proximal surface 136 may include a proximal surface of the impeller 114. As shown, the gap 134 is disposed adjacent the outlet apertures 110.

In embodiments, the gap 134 may be configured such that the rotation of the proximal surface 136 with respect to the distal-facing surface 130 may facilitate causing blood to flow into and out of the gap 134. According to embodiments, at least one washout blade (not shown in FIG. 1, but shown and described below) may be included, disposed on the proximal surface 136. The size of the gap, size of the at least one washout blade, number of washout blades, orientation of washout blades, and/or the like, may be used to configure the blood flow into and out of the gap 134. That is, for example, the size of the gap and/or the washout blades may be increased to increase the blood flow into and out of the gap 134.

Figure 2B:
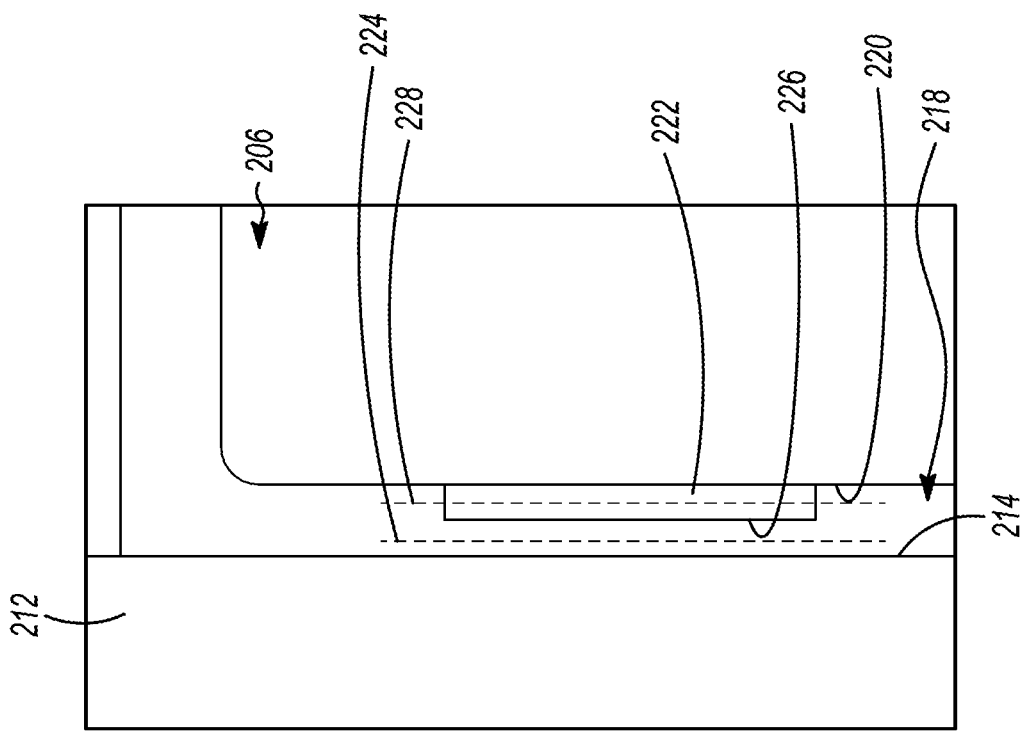
FIG. 2B depicts an enlarged version of the called out region of FIG. 2A, in accordance with embodiments of the subject matter disclosed herein.
Figure 2A:
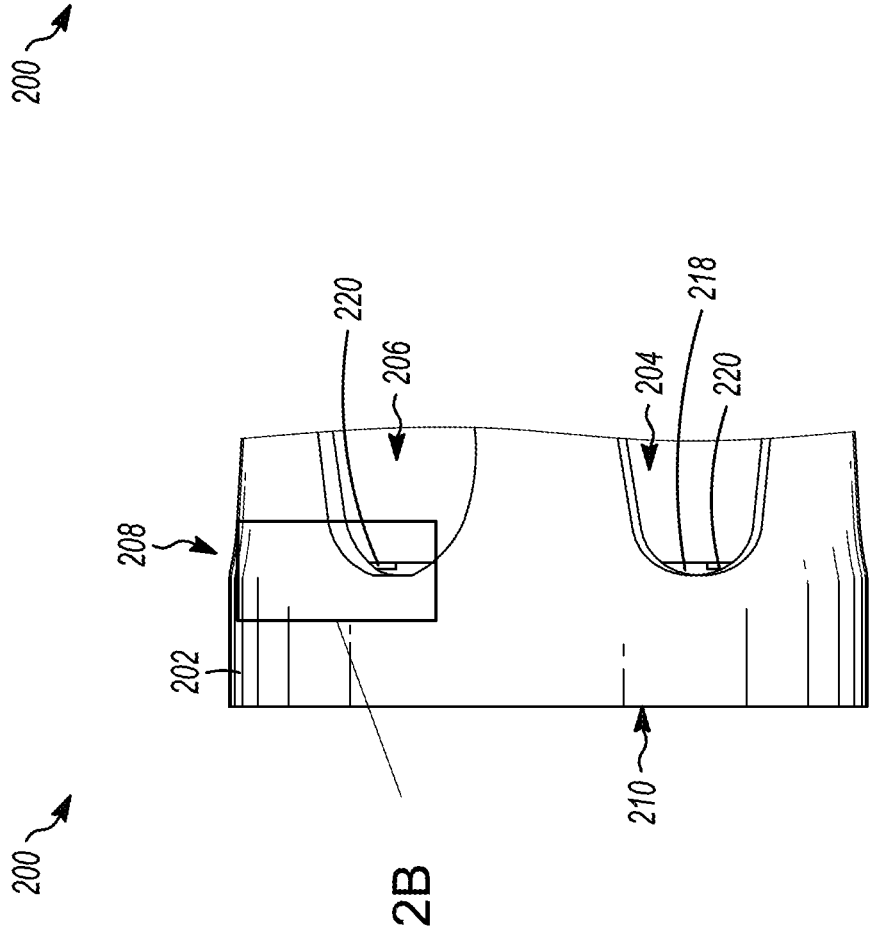
FIG. 2A depicts a partially-transparent side view of a portion of an illustrative percutaneous mechanical circulatory support device, in accordance with embodiments of the subject matter disclosed herein.
Figure 2C:
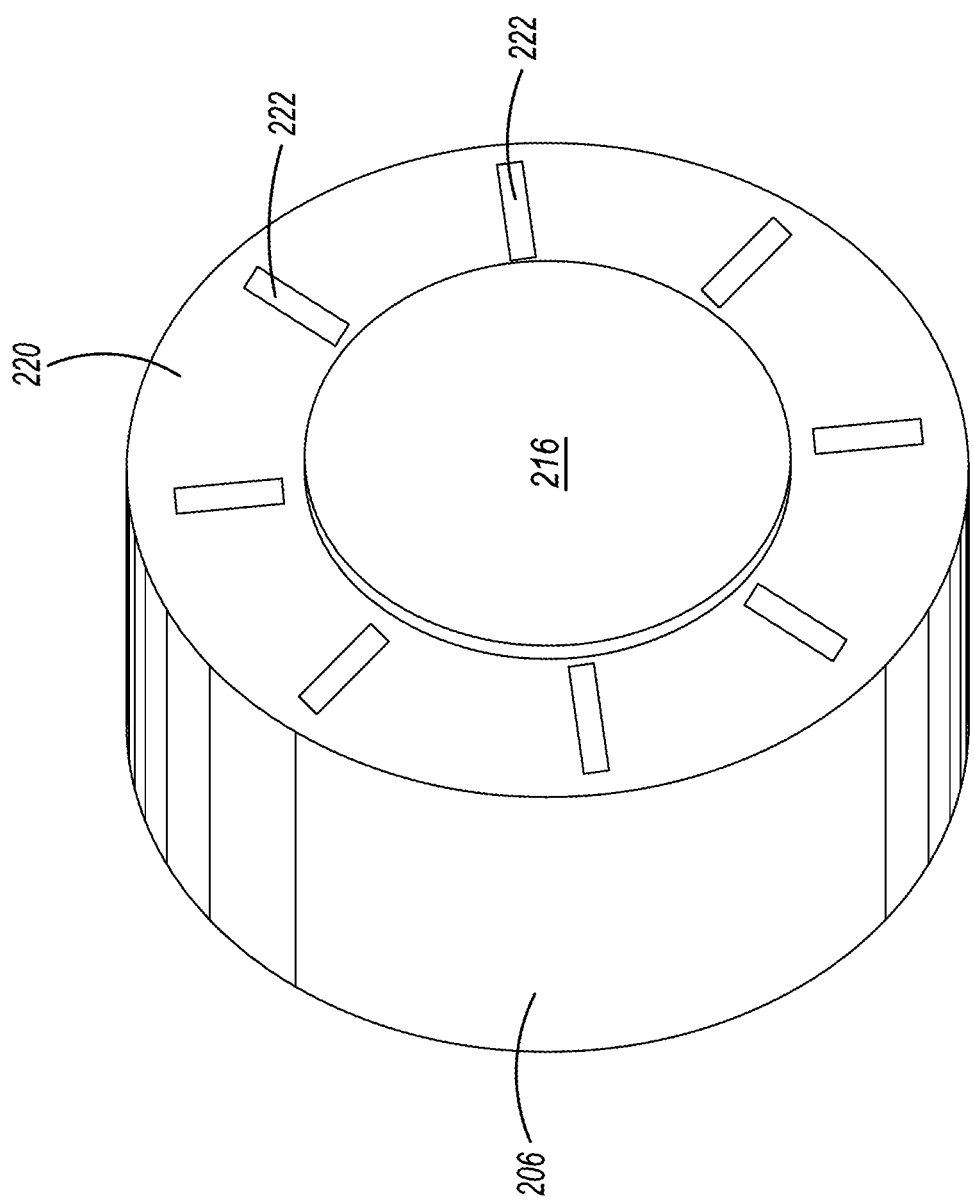
FIG. 2C is a perspective view of a portion of an impeller assembly of the support device depicted in FIG. 2A, in accordance with embodiments of the subject matter disclosed herein.

As indicated above, any number of different types of configurations may be used in implementing aspects of the embodiments of the washout blades described above, with reference to FIGS. 1A and 1B. An illustrative implementation is shown in FIGS. 2A-2C. FIG. 2A depicts a partially-transparent side view of a portion of an illustrative percutaneous mechanical circulatory support device 200 (also referred to herein, interchangeably, as a "blood pump"), in accordance with embodiments of the subject matter disclosed herein; FIG. 2B depicts an enlarged version of the called out region of FIG. 2A, in accordance with embodiments of the subject matter disclosed herein; and FIG. 2C is a perspective view of a portion of an impeller assembly of the device 200 depicted in FIGS. 2A and 2B, in accordance with embodiments of the subject matter disclosed herein. According to embodiments, the circulatory support device 200 may be, or be similar to, the circulatory support device 100 depicted in FIGS. 1A and 1B.

As shown, the circulatory support device 200 includes an impeller assembly housing 202 having outlet apertures 204 defined therein. An impeller assembly 206 is disposed within the impeller assembly housing 202 and is maintained in its orientation by being retained, at a first, proximal end 208, by a first (proximal) bearing assembly 210 and, at a second, distal end (not shown), by a second (distal) bearing assembly (not shown). According to embodiments, the proximal bearing assembly 210 may include a thrust plate 212 having a distal-facing surface 214, a portion of which is configured to engage an impeller bearing surface 216. A gap 218 may be formed between the distal-facing surface 214 and a proximal surface 220 of the impeller assembly 206. In embodiments, the proximal surface 220 may include a proximal surface of a magnet cover that is configured to be disposed over at least a proximal surface of the rotor magnet (not shown). In other embodiments (e.g., in direct-drive implementations), the proximal surface 220 may include a proximal surface of the impeller. As shown, the gap 218 is disposed adjacent the outlet apertures 204.

A number of washout blades 222 are disposed on the proximal surface 220 and configured to facilitate blood flow through the gap 218. That is, for example, the washout blades 222 are configured to facilitate blood flow into the gap 218 and out of the gap 218. According to embodiments, the blades 222 and the gap 218 may be configured so that, as the impeller assembly 206 rotates, blood is drawn into the gap 218 at least approximately along a mid-gap plane 224 (a plane that passes through points that are located equidistant from the distal-facing surface 214 and a proximal edge 226 of a blade 222) and flows out of the gap at least approximately along a mid-blade plane 228 (a plane that passes through points that are located at least approximately equidistant from the impeller bearing surface 220 and a distal edge 226 of a blade 222).

According to embodiments, the device may include only one washout blade 222, two washout blades, or more than two washout blades (e.g., 3, 4, 5, 6, 7, 8, or more). One or more of the washout blades may extend radially outward and may be straight, angled, and/or curved. In embodiments, one or more of the washout blades may be forward-swept with respect to a direction of rotation of the impeller bearing surface, backward-swept with respect to the direction of the rotation of the impeller bearing surface, and/or the like. Any one or more of the washout blades may be configured to have any number of different sizes, shapes, and/or the like. For example, in embodiments, a height of at least one washout blade, which is a distance from the impeller bearing surface to a proximal edge of the washout blade, may be approximately half the width of the gap. In embodiments, the height of the washout blade may be greater than half the width of the gap, less than half the width of the gap, variable along a length of the washout blade, and/or the like.

In embodiments, the impeller bearing surface may be, or include, a proximal surface of a magnet cover that is configured to be disposed over at least a portion of the rotor magnet. In other embodiments, the impeller bearing surface may be a proximal surface of the impeller itself such as, for example, in direct drive configurations. For example, in embodiments, washout blades may be integrated into a magnet cover, an impeller surface, and/or the like. According to embodiments, the blood flow into, and out of, the gap may be configured (e.g, increased, decreased, set to a certain level or range of levels, optimized, and/or the like, by selecting a certain number of washout blades, a certain width of the gap, and/or the like.

The illustrative circulatory support device 200 shown in FIGS. 2A-2C is not intended to suggest any limitation as to the scope of use or functionality of embodiments of the present disclosure. The illustrative circulatory support device 200 also should not be interpreted as having any dependency or requirement related to any single component or combination of components illustrated therein. Additionally, various components depicted in FIGS. 2A-2C may be, in embodiments, integrated with various ones of the other components depicted therein (and/or components not illustrated), all of which are considered to be within the ambit of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A blood pump, comprising:
   a housing;
   an impeller assembly disposed within the housing, the impeller assembly comprising:
     a proximal-facing surface;
     a drive shaft being rotatable relative to the housing, the drive shaft comprising a proximal-facing bearing surface;
     an impeller coupled to and configured to rotate with the drive shaft relative to the housing:
   a motor configured to drive the drive shaft and the impeller; and
   a thrust plate disposed adjacent the motor, the thrust plate having a distal-facing surface and being in contact with the proximal-facing bearing surface of the drive shaft,
     wherein the proximal-facing surface of the impeller assembly is disposed adjacent the distal-facing surface of the thrust plate such that a gap is defined between the proximal-facing surface of the impeller assembly and the distal-facing surface of the thrust plate, and the proximal-facing surface of the impeller assembly has disposed thereon at least one washout blade configured to facilitate blood flow through the gap.

2. The blood pump of claim 1, wherein the at least one washout blade comprises two or more washout blades.

3. The blood pump of claim 1, wherein the at least one washout blade extends radially outward.

4. The blood pump of claim 1, wherein the proximal-facing surface of the impeller assembly comprises a proximal surface of a magnet cover that is configured to be disposed over at least a proximal surface of a rotor magnet.

5. The blood pump of claim 1, wherein a height of the at least one washout blade, comprising a distance from the proximal-facing surface of the impeller assembly to a proximal edge of the at least one washout blade, is approximately half the width of the gap.

6. The blood pump of claim 1, wherein the bearing surface of the drive shaft is a convex surface.

7. The blood pump of claim 1, wherein the proximal-facing bearing surface of the drive shaft is in direct rotational contact with the distal-facing surface of the thrust plate.

8. The blood pump of claim 1, wherein the impeller assembly is retained within the housing by a proximal bearing assembly and a distal bearing assembly, and the impeller assembly is rotatable relative to the proximal bearing assembly and the distal bearing assembly.

9. The blood pump of claim 8, wherein the proximal bearing assembly includes the thrust plate.

10. The blood pump of claim 8, wherein the proximal bearing assembly is adjacent a proximal end of the drive shaft and the distal bearing assembly is adjacent a distal end of the drive shaft.

11. A blood pump, comprising:

a housing;

an impeller assembly disposed within the housing, the impeller assembly comprising: a proximal-facing surface;
- a drive shaft being rotatable relative to the housing, the drive shaft comprising a proximal-facing bearing surface;
- an impeller coupled to and configured to rotate with the drive shaft relative to the housing:

a motor configured to drive the drive shaft and the impeller; and a thrust plate disposed adjacent the motor, the thrust plate having a distal-facing surface and being in contact with the proximal-facing bearing surface of the drive shaft, wherein the proximal-facing surface of the impeller assembly is disposed adjacent the distal-facing surface of the thrust plate such that a gap is defined between the proximal-facing surface of the impeller assembly and the distal-facing surface of the thrust plate, and the proximal-facing surface of the impeller assembly has disposed thereon two or more washout blades configured to facilitate blood flow through the gap, wherein the width of the gap is configured to maximize the blood flow through the gap.

12. The blood pump of claim 11, wherein the two or more washout blades extend radially outward.

13. The blood pump of claim 11, wherein the proximal-facing surface of the impeller assembly comprises a proximal surface of a magnet cover that is configured to be disposed over at least a proximal surface of a rotor magnet.

14. The blood pump of claim 11, wherein a height of the two or more washout blades, comprising a distance from the proximal-facing surface of the impeller assembly to a proximal edge of the two or more washout blades, is approximately half the width of the gap.

15. The blood pump of claim 11, wherein the bearing surface of the drive shaft is a convex surface.

16. The blood pump of claim 11, wherein the proximal-facing bearing surface of the drive shaft is in direct rotational contact with the distal-facing surface of the thrust plate.

17. The blood pump of claim 11, wherein the impeller assembly is retained within the housing by a proximal bearing assembly and a distal bearing assembly, and the impeller assembly is rotatable relative to the proximal bearing assembly and the distal bearing assembly.

18. The blood pump of claim 17, wherein the proximal bearing assembly includes the thrust plate.

19. The blood pump of claim 17, wherein the proximal bearing assembly is adjacent a proximal end of the drive shaft and the distal bearing assembly is adjacent a distal end of the drive shaft.

* * * * *